(12) United States Patent
Leroy et al.

(10) Patent No.: US 8,609,076 B2
(45) Date of Patent: Dec. 17, 2013

(54) USE OF PARTICULAR POLYOLS FOR PREVENTING THE HAIR FROM BREAKING, COMPOSITION COMPRISING THEM AND COSMETIC HAIR TREATMENT PROCESS

(75) Inventors: Frederic Leroy, Saint-Cloud (FR); Michel Philippe, Wissous (FR); Philippe Barbarat, Bois-Colombes (FR); Christian Blaise, Saint Mande (FR)

(73) Assignee: L'Oreal, Paris (FR)

( * ) Notice: Subject to any disclaimer, the term of this patent is extended or adjusted under 35 U.S.C. 154(b) by 1549 days.

(21) Appl. No.: 11/128,362

(22) Filed: May 13, 2005

(65) Prior Publication Data

US 2006/0039879 A1   Feb. 23, 2006

Related U.S. Application Data

(60) Provisional application No. 60/580,717, filed on Jun. 21, 2004.

(30) Foreign Application Priority Data

May 13, 2004 (FR) ...................................... 04 05204

(51) Int. Cl.
  *A61Q 5/00*   (2006.01)
(52) U.S. Cl.
  USPC .......... 424/70.1; 514/600; 514/601; 514/706; 514/712; 564/79; 564/95; 568/27; 568/28; 568/46
(58) Field of Classification Search
  None
  See application file for complete search history.

(56) References Cited

U.S. PATENT DOCUMENTS

| 4,035,510 A | 7/1977 | Van Scott et al. |
| 6,492,455 B1 | 12/2002 | Nadolsky |
| 2005/0113269 A1* | 5/2005 | Landa et al. ................. 510/130 |

FOREIGN PATENT DOCUMENTS

| EP | 0 145 618 | 6/1985 |
| FR | 1 527 085 | 5/1968 |
| FR | 2 604 625 | 4/1988 |
| GB | 915 574 | 1/1963 |
| GB | 1 179 031 | 1/1970 |

OTHER PUBLICATIONS

Database Caplus, Chemical Abstracts Service, Database Accession No. 1996:11413; XP002308157.

* cited by examiner

*Primary Examiner* — Daniel Sullivan
*Assistant Examiner* — Barbara Frazier
(74) *Attorney, Agent, or Firm* — Oblon, Spivak, McClelland, Maier & Neustadt, L.L.P.

(57) ABSTRACT

The present invention relates to the use of polyols of formula (I):

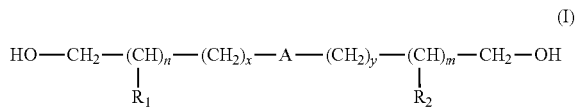

or a salt thereof, for preventing the hair from breaking.
The invention also relates to a cosmetic composition comprising at least one such polyol or a salt thereof, in a cosmetically acceptable medium, and also to a cosmetic hair treatment process using the said composition.

14 Claims, No Drawings

USE OF PARTICULAR POLYOLS FOR PREVENTING THE HAIR FROM BREAKING, COMPOSITION COMPRISING THEM AND COSMETIC HAIR TREATMENT PROCESS

REFERENCE TO PRIOR APPLICATIONS

This application claims priority to U.S. provisional application 60/580,717 filed Jun. 21, 2004, and to French patent application 0405204 filed May 13, 2004, both incorporated herein by reference.

FIELD OF THE INVENTION

The present invention relates to the use of particular polyols for preventing the hair from breaking, in particular African hair, to a cosmetic composition comprising such polyols and to a treatment process using this composition.

BACKGROUND OF THE INVENTION

In the field of haircare, problems of breakage may arise for the hair, especially for certain types of hair such as African hair. These problems of breakage generally arise during a simple mechanical treatment, for instance brushing, combing or smoothing, this mechanical treatment also possibly being performed during or after cosmetic treatments, for instance relaxing, shampooing, dyeing or permanent-waving of the hair. However, there is not at the present time any preventive treatment that is effective in preventing or limiting this problem, either on natural or treated hair.

Treatments with aqueous solutions of a humectant, such as glycerol, glycerol combined with urea, a poly(acrylic acid), dimethyl sulfoxide (or DMSO) and a poly(acrylic acid) combined with DMSO, have been described in the article published in *J. Soc. Cosmet. Chem.* 36, January/February 1985, 39-52. These treatments, and especially those based on poly(acrylic acid) or glycerol, have proved to be effective in improving the mechanical strength of Negroid hair and in reducing its level of premature breakage, i.e. its level of breakage for small elongations.

SUMMARY OF THE INVENTION

The Applicant has discovered, surprisingly, that the use of certain polyols in the haircare field, on natural or treated hair, makes it possible to prevent it from breaking and thus to improve the mechanical strength of the hair.

These polyols are especially described in patent application U.S. Pat. No. 4,546,121 as flame retardants in polyurethane foams, and in patent application WO 98/30627 as polymer crosslinking agents.

One subject of the invention is thus the use of the polyols or salts thereof as described below for preventing the hair from breaking.

Another subject of the invention is a cosmetic composition comprising at least one polyol as described below, or a salt thereof.

A subject of the invention is also a cosmetic treatment process using said composition.

Other subjects, characteristics, aspects and advantages of the invention will emerge even more clearly on reading the description and the examples that follow.

DETAILED DESCRIPTION OF THE PREFERRED EMBODIMENTS

According to the invention, the polyols used for preventing the hair from breaking correspond to formula (I) below:

$$HO-CH_2-(CH)_n-(CH_2)_x-A-(CH_2)_y-(CH)_m-CH_2-OH \quad (I)$$
$$\phantom{HO-CH_2-(CH)_n}|\phantom{-(CH_2)_x-A-(CH_2)_y-}|$$
$$\phantom{HO-CH_2-(CH)_nxxx}R_1\phantom{-(CH_2)_x-A-(CH_2)_y-}R_2$$

in which:
m and n each represent, independently of each other, an integer ranging from 0 to 6 and preferably from 1 to 4,
x and y each represent, independently of each other, 0 or 1,
$R_1$ and $R_2$ each represent, independently of each other, H, OH, —COOM, a halogen atom or a $C_1$-$C_4$ alkyl or —$NR_1'R_2'$ group;
M represents a hydrogen atom, an alkali metal or alkaline-earth metal such as sodium or potassium, or a $C_1$-$C_4$ alkyl group;
$R_1'$ and $R_2'$ each represent, independently of each other, H or a $C_1$-$C_4$ alkyl group;
A represents:

$$-NR_3-\overset{O}{\underset{\|}{C}}-NR_4-,\quad -\overset{O}{\underset{\underset{\|}{O}}{\overset{\|}{S}}}-,\quad -\overset{O}{\underset{\|}{S}}-,$$

$$-\overset{O}{\underset{\|}{C}}-,\quad -S-,\quad -O-,\quad -\underset{\underset{R_5}{|}}{N}-,$$

$$-\overset{+}{\underset{\underset{R_6}{|}}{\overset{R_5}{\underset{|}{N}}}}-,\quad -\overset{O}{\underset{\|}{C}}-O-,\quad -NH-\overset{O}{\underset{\|}{C}}-,$$

$$-NH-\overset{O}{\underset{\|}{C}}-O-,\quad -NH-\overset{O}{\underset{\underset{\|}{O}}{\overset{\|}{S}}}-,$$

$$-NH-\overset{O}{\underset{\underset{\|}{O}}{\overset{\|}{S}}}-NH-,\quad -NH-\overset{O}{\underset{\|}{C}}-B-\overset{O}{\underset{\|}{C}}-NH-,$$

$$-NH-\overset{NH}{\underset{\|}{C}}-NH-,\quad -NH-\overset{NH}{\underset{\|}{C}}-,$$

$$-NH-\overset{NH}{\underset{\|}{C}}-NH-\overset{NH}{\underset{\|}{C}}-NH-,$$

$R_3$, $R_4$, $R_5$ and $R_6$ each represent, independently of each other, H or a $C_1$-$C_4$ alkyl group;
B represents:

$$-(CH)_p-$$
$$\phantom{-(CH)}|$$
$$\phantom{-(CH)}R_7$$

p represents an integer ranging from 0 to 6 and preferably from 0 to 4, and
$R_7$ represents H or OH, the symbols $R_7$ being identical or different when p is greater than 1.

Examples of $C_1$-$C_4$ alkyl groups that may especially be mentioned include methyl, ethyl, n-propyl, isopropyl, n-butyl and tert-butyl groups.

When the polyol of formula (I) comprises amine, amidine, guanidine and/or bisguanidine functions, they may be in the form of salts, especially in the form of hydrochlorides, sulphates or $C_2$-$C_8$ alkyl carboxylates.

The preferred compounds are those of formula (I) in which: A represents:

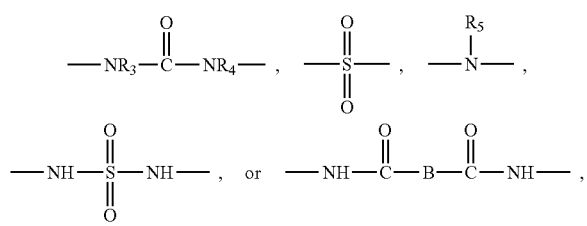

x=y=0;
$R_1=R_2=R_3=R_4=$H;
$R_5=C_1-C_4$ alkyl;
m and n have the same meanings as above;
B represents

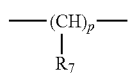

with p=0 to 2 and $R_7=$OH.

The polyols that are more particularly preferred are:

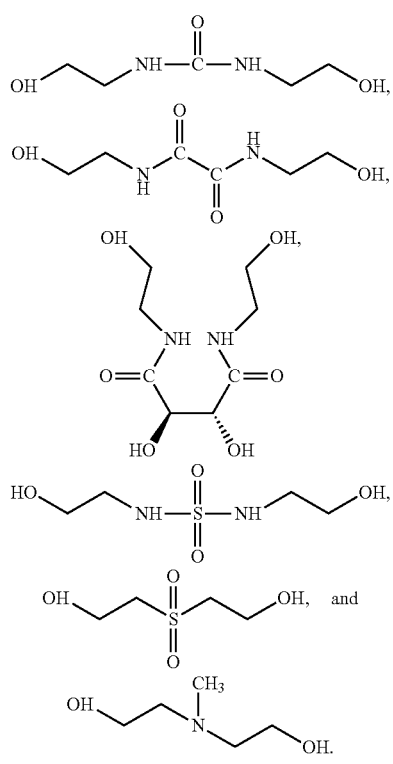

The hair towards which the invention is targeted may be of Asiatic, African or Caucasian origin, and more particularly of African origin.

Asiatic hair is generally straight and virtually round.

In contrast, African hair generally has a rather flattened and finer cross section, and forms a frizzy head of hair.

Caucasian hair has a more or less accentuated elliptical cross section and thus forms a head of hair ranging from straight to very curly, passing through wavy.

The invention thus relates to a cosmetic composition comprising, in a cosmetically acceptable medium, at least one polyol of formula (I'):

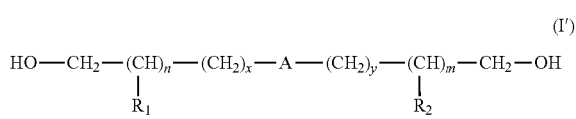

wherein:

m and n each are, independently of each other, an integer ranging from 0 to 6, and preferably from 1 to 4, x and y each represent, independently of each other, 0 or 1, $R_1$ and $R_2$ each represent, independently of each other, H, OH, —COOM, a halogen atom or a $C_1$-$C_4$ alkyl or —$NR_1'R_2'$ group;

M represents a hydrogen atom, an alkali metal or alkaline-earth metal such as sodium or potassium, or a $C_1$-$C_4$ alkyl group;

$R_1'$ and $R_2'$ each represent, independently of each other, H or a $C_1$-$C_4$ alkyl group;

A represents:

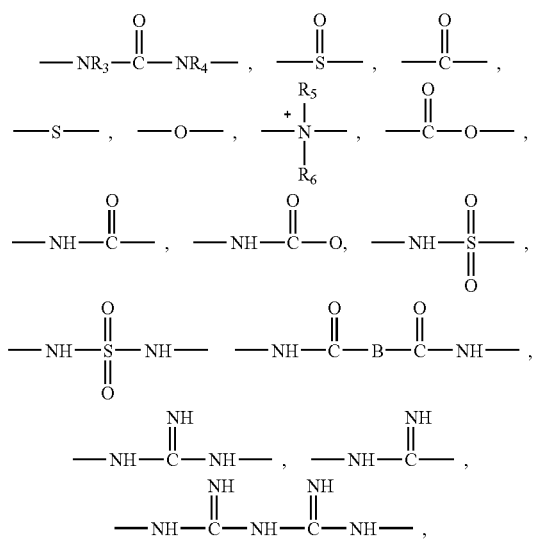

$R_3$, $R_4$, $R_5$ and $R_6$ each represent, independently of each other, H or a $C_1$-$C_4$ alkyl group;

B represents:

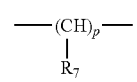

p represents an integer ranging from 1 to 6 and preferably from 1 to 4, $R_7$ represents H or OH, the symbols $R_7$ being identical or different when p is greater than 1, and at least one $R_7$ being OH, and/or salt thereof.

The salts are chosen from hydrochlorides, sulphates and $C_2$-$C_8$ alkyl carboxylates.

The polyols used preferably in the composition according to the invention are those of formula (I') wherein:

A represents:

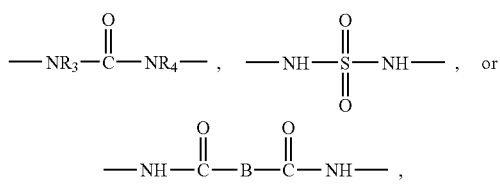

$x=y=0$;
$R_1=R_2=R_3=R_4=H$;
$R_5=C_1-C_4$ alkyl;
B represents

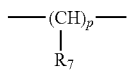

with $p=1$ or 2 and $R_7=OH$.

Most preferred compounds are chosen from

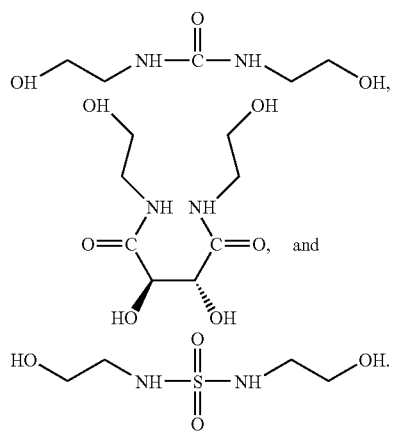

The polyol(s) or salt(s) thereof is (are) preferably contained in an amount ranging from 0.05% to 35% by weight, better still from 0.1% to 20% by weight and even more preferentially from 0.5% to 10% by weight relative to the total weight of the cosmetic composition.

For the purposes of the present invention, the term "cosmetically acceptable medium" means a medium that is compatible with the hair.

The cosmetically acceptable medium may consist solely of water or of at least one organic solvent, or alternatively of a mixture of water and of at least one organic solvent. Examples of organic solvents that may be mentioned include $C_1-C_4$ alcohols, such as ethanol and isopropanol; polyols and polyol ethers, for instance 2-butoxyethanol, propylene glycol, propylene glycol monomethyl ether, diethylene glycol monomethyl ether and diethylene glycol monoethyl ether, and also aromatic alcohols, for instance benzyl alcohol or phenoxyethanol.

The solvents are preferably present in proportions preferably of between 1% and 40% by weight approximately and even more preferably between 5% and 30% by weight approximately relative to the total weight of the cosmetic composition.

At least one additive conventionally used in cosmetics may also be added to the compositions according to the present invention. Examples of such additives that may be mentioned include anionic, cationic, nonionic, amphoteric or zwitterionic surfactants, anionic, cationic, nonionic, amphoteric or zwitterionic polymers, volatile or non-volatile, organomodified or non-organomodified silicones, mineral or organic thickeners, and in particular anionic, cationic, nonionic and amphoteric polymeric associative thickeners, antioxidants, penetrating agents, sequestering agents, fragrances, buffers, dispersants, film-forming agents, preserving agents and opacifiers.

The above additives are generally present in an amount for each of them of between 0.01% and 20% by weight relative to the weight of the final composition.

Needless to say, a person skilled in the art will take care to select this or these optional additional compound(s) such that the advantageous properties intrinsically associated with the cosmetic treatment composition in accordance with the invention are not, or are not substantially, adversely affected by the envisaged addition(s).

The pH of the cosmetic composition is generally between 3 and 12 and preferably between 5 and 11. It may be adjusted to the desired value using acidifying or basifying agents usually used in cosmetics, or alternatively using standard buffer systems.

Among the acidifying agents that may be mentioned, for example, are mineral or organic acids, for instance hydrochloric acid, orthophosphoric acid and sulfuric acid, carboxylic acids, for instance acetic acid, tartaric acid, citric acid and lactic acid, and sulfonic acids.

Among the basifying agents that may be mentioned, for example, are aqueous ammonia, alkaline carbonates, alkanolamines such as monoethanolamine, diethanolamine and triethanolamine and also derivatives thereof, sodium hydroxide, potassium hydroxide and the compounds having the following formula:

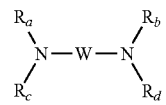

in which W is a propylene residue optionally substituted with a hydroxyl or $C_1-C_4$ alkyl group; $R_a$, $R_b$, $R_c$ and $R_d$, which may be identical or different, represent a hydrogen atom or a $C_1-C_4$ alkyl or $C_1-C_4$ hydroxyalkyl group.

The cosmetic compositions in accordance with the invention may be in the form of a lotion, a cream, a mousse, a gel, a spray or a lacquer and may be used in rinse-out or leave-in application.

The compositions in accordance with the invention may be used as haircare products, especially rinse-out or leave-in products, for preventing the hair from breaking, for example in a shampoo, a hair conditioner or a hair treatment lotion.

The present invention also relates to a cosmetic process for treating the hair, and in particular for preventing the hair from breaking, comprising the application of a cosmetic composition according to the invention to dry or wet hair, preferably at a temperature of from 10 to 60° C. and better still from 20 to 40° C., followed by optional rinsing.

The treatment may last from 5 minutes to 5 days and preferably from 10 minutes to 3 days.

The examples that follow are given as illustrations of the invention.

EXAMPLES

Example 1

Preparation of N,N'-bis(2-hydroxyethyl)urea 100 g of 2-oxazolidinone are added to 70 ml of ethanolamine. The reaction medium is heated at 150° C. for 4 hours. 200 ml of 1-butanol are then added to the medium, which is then maintained at 0° C. for 12 hours.

The precipitate is thus obtained, which is filtered off and then washed with 200 ml of heptane.

The precipitate obtained (130 g) is then taken up in 1.2 liters of acetone with vigorous stirring for 1 hour.

The precipitate is then filtered off and dried under vacuum. 70 g of a white powder are obtained (yield: 41%).

The $^1$H and $^{13}$C NMR spectra are those of N,N'-bis(2-hydroxy-ethyl)urea. An elemental analysis gave:
C: 40.30
H: 8.04
N: 18.62 and
O: 32.87.

Example 2

Preparation of 2,3-dihydroxy-N,N'-bis(2-hydroxyethyl)-butanediamide 10 g of dimethyl L-(+)-tartrate are added to a solution of 6.9 g of ethanolamine dissolved in 10 ml of methanol.

The reaction mixture is heated at 65° C. for 3 hours and is then left at room temperature for 1 hour.

The precipitate obtained is filtered off and then dried under reduced pressure.

The crude product obtained is recrystallized from a minimum amount of boiling ethanol. 8.7 g of a white powder are thus obtained (yield: 65%).

The $^1$H and $^{13}$C NMR spectra are those of 2,3-dihydroxy-N,N'-bis(2-hydroxyethyl)butanediamide. An elemental analysis gave:
C: 40.93
H: 6.87
N: 11.73 and
O: 40.59.

Example 3

Preparation of N,N'-bis(2-hydroxyethyl)oxamide

A solution of 17.2 g of ethanolamine dissolved in 20 ml of 1-hexanol is added dropwise to a suspension of 20 g of ethyl oxalate in 100 ml of 1-hexanol.

The reaction mixture is then refluxed (100° C.) for 2 hours, and the mixture is then left at room temperature for 1 hour.

The precipitate obtained is then filtered off and is recrystallized from a minimum amount of boiling ethanol. 20 g of a white powder are thus obtained (yield: 83%).

The $^1$H and $^{13}$C NMR spectra are those of N,N'-bis(2-hydroxy-ethyl)oxamide. An elemental analysis gave:
C: 40.69
H: 6.82
N: 15.72 and
O: 36.42

Example 4

Preparation of N,N'-bis(2-hydroxyethyl)sulfamide 2.36 g of sulfonyl-bis-N-oxazolidinone (0.01 mol) are added to a solution of 0.90 g of sodium hydroxide (0.0225 mol) dissolved in 30 ml of water and 15 ml of ethanol. The reaction medium is maintained at room temperature for 72 hours.

Ethanol is then evaporated off under reduced pressure and the reaction medium is then neutralized at a temperature in the region of 5° C. by dropwise addition of 1N hydrochloric acid solution.

The reaction medium is again evaporated under reduced pressure and the residue is taken up in 150 ml of absolute ethanol.

The salts are filtered off on a sinter funnel and the filtrate is evaporated to dryness.

1.5 g of N,N'-bis(2-hydroxyethyl)sulfamide are thus obtained in the form of a translucent oil (yield: 85%).

The 400 MHz $^1$H and 100 MHz $^{13}$C NMR spectra and the mass spectrum are those of N,N'-bis(2-hydroxyethyl)sulfamide.

400 MHz $^1$H NMR, in DMSO-d6: δ: 2.87 ppm (t, 4H), 3.34 ppm (t, 4H), 5.71 ppm (bs)

100 MHz $^{13}$C NMR, in DMSO-d6: δ: 45.14 ppm, 60.28 ppm.

Example 5

The hair used for the following tests was left in a glove box at 25° C. and 45% relative humidity for about 24 hours.

A composition was prepared by mixing together 5% by weight of the compound of Example 1 and 95% by weight of water relative to the total weight of the composition.

30 natural African hairs were then treated with this composition: the hairs were immersed for 3 days at 40° C., without final rinsing, and their level of premature breakage was then compared with that of a batch of untreated natural control hairs.

Mechanical tests were performed using a Zwick tensile testing machine on the hairs 30 mm long. The hairs were drawn at a speed of 10 mm/minute.

The level of premature breakage of the treated African hair, on the one hand, and of the untreated African hair, on the other hand, was evaluated as follows:

$$R = 1 - (\text{number of hairs showing breakage under tension in the hardening zone}/N)$$

N being the total number of hairs tested.

The results are indicated in the following table:

|  | First test | Second test |
| --- | --- | --- |
| Treated hair N = 30 | R = 0.17 | R = 0.10 |
| Control hair N = 30 | R = 0.27 | R = 0.27 |

A marked decrease in the level of premature breaking of the hair treated with the composition according to the invention is observed.

The invention claimed is:

1. A method for improving the mechanical strength of human hair of African origin and/or preventing the hair from breaking, comprising applying to the hair, a composition comprising at least one polyol of formula (I) in a cosmetically acceptable medium:

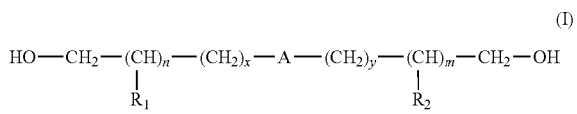

wherein:
- m and n each represent, independently of each other, an integer ranging from 0 to 6,
- x and y each represent, independently of each other, 0 or 1,
- $R_1$ and $R_2$ each represent, independently of each other, H, OH, —COOM, a halogen atom or a $C_1$-$C_4$ alkyl or —$NR_1'R_2'$ group;
- M represents a hydrogen atom, an alkali metal or alkaline-earth metal, or a $C_1$-$C_4$ alkyl group;
- $R_1'$ and $R_2'$ each represent, independently of each other, H or a $C_1$-$C_4$ alkyl group;
- A represents:

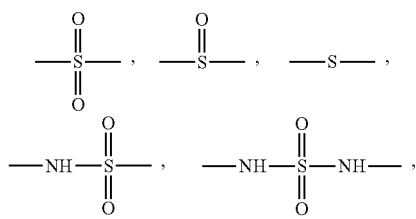

or a salt thereof.

2. The method for improving the mechanical strength of hair and/or preventing the hair from breaking according to claim 1, wherein A represents:

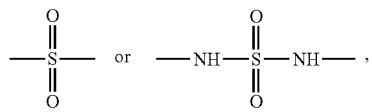

x=y=0;
$R_1$=$R_2$=H.

3. The method for improving the mechanical strength of hair and/or preventing the hair from breaking according to claim 1, wherein the at least one polyol is selected from the group consisting of:

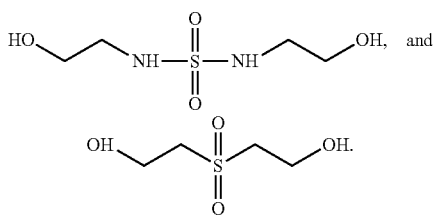

4. The method for improving the mechanical strength of hair and/or preventing the hair from breaking according to claim 1, wherein the salt thereof is selected from the group consisting of a hydrocholide, a sulfate and a $C_2$-$C_8$ alkyl carboxylate.

5. The method of claim 1, wherein the polyol(s) or salt(s) is (are) in the composition in an amount ranging from 0.05% to 35% by weight relative to the total weight of the composition.

6. The method of claim 1, wherein the polyol(s) or salt(s) is (are) in the composition in an amount ranging from 0.1% to 20% by weight relative to the total weight of the composition.

7. The method of claim 1, wherein the cosmetically acceptable medium consists of water, at least one organic solvent, or a mixture of water and of at least one organic solvent.

8. The method of claim 1, wherein the cosmetically acceptable medium comprises at least one organic solvent selected from the group consisting of a C1-C4 alcohol, a polyol, a polyol ether and an aromatic alcohol.

9. The method of claim 8, wherein the organic solvent is ethanol, isopropanol, 2-butoxyethanol, propylene glycol, propylene glycol monomethyl ether, diethylene glycol monomethyl ether, diethylene glycol monoethyl ether, benzyl alcohol or phenoxyethanol.

10. The method of claim 1, wherein the composition comprises at least one additive selected from the group consisting of anionic, cationic, nonionic, amphoteric or zwitterionic surfactants, anionic, cationic, nonionic, amphoteric or zwitterionic polymers, volatile or non-volatile, organomodified or non- organomodified silicones, mineral or organic thickeners, antioxidants, penetrating agents, sequestering agents, fragrances, buffers, dispersants, film-forming agents, preserving agents and opacifiers.

11. The method for improving the mechanical strength of hair and/or preventing the hair from breaking according to claim 1, further comprising rinsing the hair after application of the composition.

12. The method for improving the mechanical strength of hair and/or preventing the hair from breaking according to claim 1, wherein application occurs at a temperature ranging from 10 to 60° C.

13. The method for improving the mechanical strength of hair and/or preventing the hair from breaking according to claim 1, wherein treatment lasts from 5 minutes to 5 days.

14. A method for improving the mechanical strength of human hair and/or preventing the hair from breaking, comprising applying to the hair, a composition comprising at least one polyol of formula (I) in a cosmetically acceptable medium:

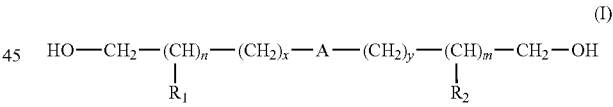

wherein:
- m and n each represent, independently of each other, an integer ranging from 0 to 6,
- x and y each represent, independently of each other, 0 or 1,
- $R_1$ and $R_2$ each represent, independently of each other, H, OH, —COOM, a halogen atom or a $C_1$-$C_4$ alkyl or — $NR_1'R_2'$ group;
- M represents a hydrogen atom, an alkali metal or alkaline-earth metal, or a $C_1$-$C_4$ alkyl group;
- $R_1'$ and $R_2'$ each represent, independently of each other, H or a $C_1$-$C_4$ alkyl group;
- A represents:

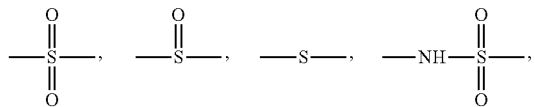

-continued
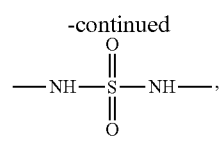
or a salt thereof.
* * * * *